US008153144B2

(12) United States Patent
Berry et al.

(10) Patent No.: US 8,153,144 B2
(45) Date of Patent: *Apr. 10, 2012

(54) STABLE MULTIPHASE COMPOSITION COMPRISING ALKYLAMPHOACETATE

(75) Inventors: Jamal Ihsan Berry, Hamilton, OH (US); Karl Shiqing Wei, Mason, OH (US); Edward Dewey Smith, III, Mason, OH (US); Scott William Syfert, Ft. Mitchell, KY (US)

(73) Assignee: The Proctor & Gamble Company, Cincinnati, OH (US)

( * ) Notice: Subject to any disclaimer, the term of this patent is extended or adjusted under 35 U.S.C. 154(b) by 634 days.

This patent is subject to a terminal disclaimer.

(21) Appl. No.: 11/710,181

(22) Filed: Feb. 23, 2007

(65) Prior Publication Data

US 2007/0248562 A1    Oct. 25, 2007

Related U.S. Application Data

(60) Provisional application No. 60/777,643, filed on Feb. 28, 2006.

(51) Int. Cl.
*A61K 8/02* (2006.01)
*A61K 31/74* (2006.01)
*A61K 8/00* (2006.01)

(52) U.S. Cl. ............ 424/401; 424/78.02; 510/130

(58) Field of Classification Search ........... 424/401, 424/78.02; 510/130
See application file for complete search history.

(56) References Cited

U.S. PATENT DOCUMENTS

| | | | |
|---|---|---|---|
| 2,020,454 A | 11/1935 | Bisbee et al. | |
| 2,438,091 A | 3/1948 | Lynch | |
| 2,528,378 A | 10/1950 | Mannheimer | |
| 2,658,072 A | 11/1953 | Kosmin | |
| 2,798,053 A | 7/1957 | Brown | |
| 2,986,271 A | 5/1961 | Forrer | |
| 3,455,440 A | 7/1969 | West | |
| 3,479,429 A | 11/1969 | Morshauser et al. | |
| 3,533,955 A | 10/1970 | Pader et al. | |
| 3,542,256 A | 11/1970 | Waterman | |
| 3,615,972 A | 10/1971 | Morehouse, Jr. et al. | |
| 3,618,757 A | 11/1971 | Funkhouser | |
| 3,800,998 A | 4/1974 | Gask | |
| 3,850,365 A | 11/1974 | Dietrich | |
| 3,899,076 A | 8/1975 | Florian | |
| 3,929,678 A | 12/1975 | Laughlin et al. | |
| 3,937,811 A | 2/1976 | Papantoniou et al. | |
| 3,951,679 A | 4/1976 | Bernhard et al. | |
| 3,980,767 A | 9/1976 | Chown et al. | |
| 4,159,028 A | 6/1979 | Barker et al. | |
| 4,263,363 A | 4/1981 | Buck et al. | |
| 4,335,103 A | 6/1982 | Barker et al. | |
| 4,379,753 A | 4/1983 | Bolich, Jr. | |
| 4,387,090 A | 6/1983 | Bolich, Jr. | |
| 4,425,322 A | 1/1984 | Harvey et al. | |
| 4,509,949 A | 4/1985 | Huang et al. | |
| 4,518,578 A | 5/1985 | Hayes et al. | |
| D292,879 S | 11/1987 | Smith | |
| 4,705,681 A | 11/1987 | Maes et al. | |
| 4,818,575 A | 4/1989 | Hirata et al. | |
| 4,899,877 A | 2/1990 | Kiernan | |
| 4,966,205 A | 10/1990 | Tanaka | |
| 4,980,155 A | 12/1990 | Shah et al. | |
| 5,002,680 A | 3/1991 | Schmidt et al. | |
| 5,011,690 A | 4/1991 | Garvey et al. | |
| 5,052,557 A | 10/1991 | Contino et al. | |
| 5,059,414 A | 10/1991 | Dallal et al. | |
| 5,087,445 A | 2/1992 | Haffey et al. | |
| 5,223,315 A | 6/1993 | Katsura et al. | |
| 5,228,912 A | 7/1993 | Herget et al. | |
| 5,248,495 A | 9/1993 | Patterson et al. | |
| RE34,584 E | 4/1994 | Grote et al. | |
| 5,304,334 A | 4/1994 | Lahanas et al. | |
| 5,393,450 A | 2/1995 | Shana'a | |
| 5,451,396 A | 9/1995 | Villars | |
| 5,455,035 A | 10/1995 | Guerrero et al. | |
| 5,487,168 A | 1/1996 | Geiner et al. | |
| 5,487,884 A | 1/1996 | Bissett et al. | |
| 5,530,054 A | 6/1996 | Tse et al. | |
| 5,540,853 A | 7/1996 | Trinh et al. | |
| 5,556,628 A | 9/1996 | Derian et al. | |
| 5,578,299 A * | 11/1996 | Starch | 424/78.03 |
| 5,612,307 A | 3/1997 | Chambers et al. | |
| 5,632,420 A | 5/1997 | Lohrman et al. | |
| 5,635,171 A | 6/1997 | Nadaud | |
| 5,652,228 A | 7/1997 | Bissett | |
| 5,661,189 A | 8/1997 | Grieveson et al. | |
| 5,681,852 A | 10/1997 | Bissett | |

(Continued)

FOREIGN PATENT DOCUMENTS

CA    2246316 A1    6/1998

(Continued)

OTHER PUBLICATIONS

J. Caelles et al., "Anionic and Cationic Compounds in Mixed Systems," Cosmetics & Toiletries, vol. 106, Apr. 1991. pp. 49-54.
C.J. van Oss, "Coacervation, Complex-Coacervation and Flocculation," J. Dispersion Science and Technology, vol. 9 (5, 6), 1988-89, p. 561-573.
D.J. Burgess, "Practical Analysis of Complex Coacervate Systems," J. of Colloid Anti Interface Science, vol. 140, No. 1, Nov. 1990, pp. 227-238.
Kobo Brochure, "Treated Pigments" (May 2000).
International Search Report, PCT/IB2007/050655, dated Jul. 10, 2007 (6 pages).
Crank, Mathematics of Duffusion, 2nd Edition, p. 63, (1975).
Milton, Introduction to Probability and Statistics, 4th Edition, p. 317 (Section 9.2: Testing Hypotheses on a Proportion), (Jan. 2011).
Household Products Database, Brand Information, "Olay Daily Renewal Moisturizing Body Wash, Calming," [Online] URL: http://householdproducts.nlm.nih.gov/cgi-bin/household/brands?tbl=brands&id=16003084, accessed Feb. 8, 2006 (2 pages).

(Continued)

Primary Examiner — Kevin E Weddington

(57) ABSTRACT

The multiphase personal care composition of the present invention comprises a first phase and a second phase. The first phase is comprised of structured surfactant phase that comprises at least about 0.5% of alkylamphoacetate. The alkylamphoacetate comprises a Percentage Diacetate of less than about 15%.

20 Claims, 2 Drawing Sheets

U.S. PATENT DOCUMENTS

| | | | |
|---|---|---|---|
| 5,687,779 A | 11/1997 | Andersson et al. | |
| 5,716,920 A | 2/1998 | Glenn et al. | |
| 5,851,978 A | 12/1998 | Shana'a | |
| 5,873,494 A | 2/1999 | Dallas, Jr. | |
| 5,885,948 A | 3/1999 | Glenn, Jr. et al. | |
| 5,914,117 A | 6/1999 | Lavaud | |
| 5,925,603 A * | 7/1999 | D'Angelo | 510/119 |
| 5,929,019 A | 7/1999 | Puvvada et al. | |
| 5,932,203 A | 8/1999 | Coffindaffer et al. | |
| 5,935,561 A | 8/1999 | Inman et al. | |
| 5,947,335 A | 9/1999 | Milio et al. | |
| 5,952,286 A | 9/1999 | Puvvada et al. | |
| 5,954,213 A | 9/1999 | Gerhart et al. | |
| 5,965,500 A | 10/1999 | Puvvada | |
| 5,965,501 A | 10/1999 | Rattinger et al. | |
| 5,972,361 A * | 10/1999 | Fowler et al. | 424/402 |
| 6,051,541 A | 4/2000 | Neuser et al. | |
| D426,158 S | 6/2000 | Flurer et al. | |
| 6,080,707 A | 6/2000 | Glenn, Jr. et al. | |
| 6,114,290 A | 9/2000 | Lyle et al. | |
| 6,174,845 B1 | 1/2001 | Rattinger et al. | |
| 6,176,391 B1 | 1/2001 | Rehkemper et al. | |
| 6,176,395 B1 | 1/2001 | Abbott et al. | |
| 6,190,648 B1 | 2/2001 | Kouzu et al. | |
| 6,194,364 B1 | 2/2001 | Glenn, Jr. | |
| D438,460 S | 3/2001 | Hammond | |
| D439,165 S | 3/2001 | Erckelbout et al. | |
| 6,213,166 B1 | 4/2001 | Thibiant et al. | |
| D441,645 S | 5/2001 | Longhurst | |
| 6,232,496 B1 * | 5/2001 | Carr et al. | 562/564 |
| 6,245,323 B1 | 6/2001 | Christie et al. | |
| 6,245,344 B1 | 6/2001 | Thibiant et al. | |
| 6,255,264 B1 | 7/2001 | Fleurot et al. | |
| 6,267,978 B1 | 7/2001 | Sang et al. | |
| 6,268,322 B1 | 7/2001 | St. Lewis et al. | |
| 6,294,179 B1 | 9/2001 | Lee et al. | |
| 6,306,806 B1 | 10/2001 | St. Lewis et al. | |
| 6,335,312 B1 | 1/2002 | Coffindaffer et al. | |
| 6,340,723 B1 | 1/2002 | Nitta et al. | |
| 6,362,156 B1 | 3/2002 | Hsu et al. | |
| D455,655 S | 4/2002 | Bunce | |
| 6,367,519 B2 | 4/2002 | Thibiant et al. | |
| 6,383,999 B1 | 5/2002 | Coyle et al. | |
| 6,385,992 B1 | 5/2002 | Flore, Jr. | |
| 6,394,323 B2 | 5/2002 | McClean et al. | |
| 6,395,691 B1 | 5/2002 | Tsaur | |
| 6,419,783 B1 | 7/2002 | Rainey et al. | |
| 6,426,326 B1 | 7/2002 | Mitra et al. | |
| 6,429,177 B1 | 8/2002 | Williams et al. | |
| 6,491,932 B1 | 12/2002 | Ramin et al. | |
| 6,495,498 B2 | 12/2002 | Niemiec et al. | |
| 6,506,391 B1 | 1/2003 | Biatry | |
| 6,516,838 B2 | 2/2003 | Thibiant et al. | |
| 6,517,939 B1 | 2/2003 | Moini et al. | |
| 6,521,216 B1 | 2/2003 | Glandorf et al. | |
| 6,533,873 B1 | 3/2003 | Margosiak et al. | |
| 6,534,456 B2 | 3/2003 | Hayward et al. | |
| 6,534,457 B2 | 3/2003 | Mitra | |
| 6,547,063 B1 * | 4/2003 | Zaveri et al. | 206/219 |
| 6,555,509 B2 | 4/2003 | Abbas et al. | |
| 6,564,978 B1 | 5/2003 | Safian et al. | |
| 6,574,985 B2 | 6/2003 | Fiore, Jr. | |
| 6,589,509 B2 | 7/2003 | Keller et al. | |
| 6,645,511 B2 | 11/2003 | Aronson et al. | |
| 6,652,134 B2 | 11/2003 | Lloyd | |
| 6,663,855 B2 | 12/2003 | Frechet et al. | |
| 6,673,371 B2 | 1/2004 | Brown et al. | |
| 6,673,755 B2 | 1/2004 | Wei et al. | |
| 6,682,726 B2 | 1/2004 | Marchesi et al. | |
| D486,395 S | 2/2004 | Lovell et al. | |
| D486,398 S | 2/2004 | Lovell et al. | |
| 6,691,394 B1 | 2/2004 | McClean | |
| 6,695,510 B1 | 2/2004 | Look et al. | |
| 6,699,488 B2 | 3/2004 | Deckner et al. | |
| 6,759,376 B2 | 7/2004 | Zhang et al. | |
| 6,764,991 B2 | 7/2004 | Puvvada et al. | |
| 6,773,811 B2 | 8/2004 | Ferguson et al. | |
| 6,780,826 B2 | 8/2004 | Zhang et al. | |
| 6,787,511 B2 | 9/2004 | Patel et al. | |
| 6,797,683 B2 | 9/2004 | Shana'a et al. | |
| 6,903,057 B1 | 6/2005 | Tsaur | |
| 6,919,303 B2 | 7/2005 | Pham et al. | |
| 6,924,256 B2 | 8/2005 | Massaro et al. | |
| 7,143,893 B2 | 12/2006 | Kelly | |
| 7,144,542 B2 | 12/2006 | Holzer et al. | |
| 7,273,837 B2 | 9/2007 | Boutique et al. | |
| 7,511,003 B2 * | 3/2009 | Focht et al. | 510/130 |
| 7,524,807 B2 | 4/2009 | Clapp et al. | |
| 7,666,825 B2 | 2/2010 | Wagner et al. | |
| 2001/0036467 A1 | 11/2001 | Thibiant et al. | |
| 2002/0004468 A1 | 1/2002 | Hodge et al. | |
| 2002/0010110 A1 | 1/2002 | Hayward et al. | |
| 2003/0003069 A1 | 1/2003 | Carson et al. | |
| 2003/0049282 A1 | 3/2003 | Aaronson et al. | |
| 2003/0054019 A1 | 3/2003 | Aronson et al. | |
| 2003/0068287 A1 | 4/2003 | Ansara et al. | |
| 2003/0152540 A1 | 8/2003 | Putman et al. | |
| 2003/0161852 A1 | 8/2003 | Miller et al. | |
| 2003/0180246 A1 | 9/2003 | Frantz et al. | |
| 2003/0222100 A1 | 12/2003 | Husband et al. | |
| 2004/0033914 A1 | 2/2004 | Patel et al. | |
| 2004/0048757 A1 | 3/2004 | Zhang et al. | |
| 2004/0048758 A1 | 3/2004 | Zhang et al. | |
| 2004/0057920 A1 | 3/2004 | Focht et al. | |
| 2004/0058920 A1 | 3/2004 | Jover et al. | |
| 2004/0091445 A1 | 5/2004 | Dykstra et al. | |
| 2004/0092415 A1 | 5/2004 | Focht et al. | |
| 2004/0105827 A1 | 6/2004 | Grimm et al. | |
| 2004/0146475 A1 | 7/2004 | Peffly et al. | |
| 2004/0158940 A1 | 8/2004 | Wells et al. | |
| 2004/0180020 A1 | 9/2004 | Manelski et al. | |
| 2004/0219119 A1 | 11/2004 | Wei et al. | |
| 2004/0223929 A1 | 11/2004 | Clapp et al. | |
| 2004/0223939 A1 | 11/2004 | Clausen et al. | |
| 2004/0223991 A1 | 11/2004 | Wei et al. | |
| 2004/0223992 A1 | 11/2004 | Clapp et al. | |
| 2004/0232023 A1 | 11/2004 | Bansal et al. | |
| 2004/0235693 A1 | 11/2004 | Wei et al. | |
| 2004/0242706 A1 | 12/2004 | Wiersema et al. | |
| 2004/0248748 A1 | 12/2004 | Wei et al. | |
| 2004/0248749 A1 | 12/2004 | Mitra et al. | |
| 2005/0003975 A1 | 1/2005 | Browne et al. | |
| 2005/0020468 A1 | 1/2005 | Frantz et al. | |
| 2005/0100570 A1 | 5/2005 | Wei et al. | |
| 2005/0139574 A1 | 6/2005 | Simone et al. | |
| 2005/0143269 A1 | 6/2005 | Wei et al. | |
| 2005/0191449 A1 | 9/2005 | Funato et al. | |
| 2005/0192187 A1 | 9/2005 | Wagner et al. | |
| 2005/0192188 A1 | 9/2005 | Wagner et al. | |
| 2005/0192189 A1 | 9/2005 | Wagner et al. | |
| 2005/0238680 A1 | 10/2005 | Stella et al. | |
| 2005/0249758 A1 | 11/2005 | Di Puccio Pagano | |
| 2005/0269372 A1 | 12/2005 | Smith | |
| 2005/0276768 A1 | 12/2005 | Wei et al. | |
| 2006/0002880 A1 | 1/2006 | Peffly et al. | |
| 2006/0008438 A1 | 1/2006 | Velarde et al. | |
| 2006/0079419 A1 | 4/2006 | Wagner et al. | |
| 2006/0079420 A1 | 4/2006 | Wagner et al. | |
| 2006/0094628 A1 | 5/2006 | Wei et al. | |
| 2006/0102654 A1 | 5/2006 | Seys et al. | |
| 2006/0118139 A1 | 6/2006 | Fausnight et al. | |
| 2006/0182699 A1 | 8/2006 | Taylor et al. | |
| 2006/0191589 A1 | 8/2006 | McCall et al. | |
| 2006/0210505 A1 | 9/2006 | Clapp et al. | |
| 2006/0252662 A1 | 11/2006 | Soffin et al. | |
| 2006/0276357 A1 | 12/2006 | Smith et al. | |
| 2007/0072781 A1 | 3/2007 | Soffin et al. | |
| 2007/0141001 A1 | 6/2007 | Clapp et al. | |
| 2007/0155637 A1 | 7/2007 | Smith et al. | |
| 2007/0163990 A1 | 7/2007 | Escobosa et al. | |
| 2007/0167338 A1 | 7/2007 | McHugh et al. | |
| 2007/0187274 A1 | 8/2007 | Dalea et al. | |
| 2007/0280976 A1 | 12/2007 | Taylor et al. | |
| 2010/0209374 A1 | 8/2010 | Wei et al. | |

FOREIGN PATENT DOCUMENTS

| | | | |
|---|---|---|---|
| CH | 678488 | A5 | 9/1991 |
| DE | 19650952 | A1 | 6/1998 |
| DE | 19854086 | A1 | 5/2000 |
| EP | 0056219 | A1 | 7/1982 |
| EP | 0078138 | A2 | 5/1983 |
| EP | 0112807 | A2 | 7/1984 |
| EP | 0320473 | A1 | 6/1989 |
| EP | 0348372 | A2 | 12/1989 |
| EP | 0331617 | B1 | 4/1992 |
| EP | 0486080 | A2 | 5/1992 |
| EP | 1064918 | A1 | 1/2001 |
| EP | 1108421 | A2 | 6/2001 |
| EP | 1005849 | B1 | 9/2001 |
| EP | 1174360 | A1 | 1/2002 |
| EP | 0907345 | B1 | 5/2003 |
| EP | 1529517 | A2 | 5/2005 |
| GB | 1277324 | A | 6/1972 |
| GB | 2310398 | A | 8/1997 |
| JP | 02184884 | | 7/1990 |
| JP | 05254528 | | 10/1993 |
| JP | 2000-229817 | A | 8/2000 |
| JP | 2002-128639 | A | 5/2002 |
| JP | 2002-138010 | A | 5/2002 |
| WO | WO-90/13283 | A1 | 11/1990 |
| WO | WO-92/12212 | A1 | 7/1992 |
| WO | WO-94/10973 | A1 | 5/1994 |
| WO | WO-97/17938 | A1 | 5/1997 |
| WO | WO-98/27193 | A1 | 6/1998 |
| WO | WO-99/09952 | A1 | 3/1999 |
| WO | WO-99/38489 | A1 | 8/1999 |
| WO | WO-99/38491 | A1 | 8/1999 |
| WO | WO 00/75240 | A1 | 12/2000 |
| WO | WO-01/01931 | A2 | 1/2001 |
| WO | WO 01/23517 | A1 | 4/2001 |
| WO | WO-01/64180 | A1 | 9/2001 |
| WO | WO-01/70193 | A2 | 9/2001 |
| WO | WO-01/70926 | A1 | 9/2001 |
| WO | WO-02/100358 | A1 | 12/2002 |
| WO | WO-03/055456 | A1 | 7/2003 |
| WO | WO-03/105796 | A1 | 12/2003 |
| WO | WO-2004/018609 | A1 | 3/2004 |
| WO | WO-2004/026276 | A1 | 4/2004 |
| WO | WO-2004/050055 | A1 | 6/2004 |
| WO | WO-2004/083351 | A1 | 9/2004 |
| WO | WO-2004/096162 | A2 | 11/2004 |
| WO | WO-2004/098559 | A2 | 11/2004 |
| WO | WO-2004/100919 | A1 | 11/2004 |
| WO | WO-2005/048959 | A1 | 6/2005 |
| WO | WO-2005/065638 | A1 | 7/2005 |
| WO | WO-2005/067875 | A1 | 7/2005 |
| WO | WO-2005/084614 | A1 | 9/2005 |
| WO | WO-2005/084616 | A1 | 9/2005 |
| WO | WO-2005/123031 | A1 | 12/2005 |

OTHER PUBLICATIONS

XP002332778 "Dove All Day Moisturizing Body Wash" [Online] URL: http://www.ewg.org/reports/skindeep2/report/pht?type—PRODUCT&id=8801874, accessed Feb. 8, 2006 (6 pages).

C.D. Vaughan, "Solubility, Effects in Product, Package, Penetration and Preservation," Cosmetics and Toiletries, vol. 103, Oct. 1988.

CTFA International Cosmetic Ingredient Dictionary, Fourth Edition, 1991, pp. 12 and 80.

* cited by examiner

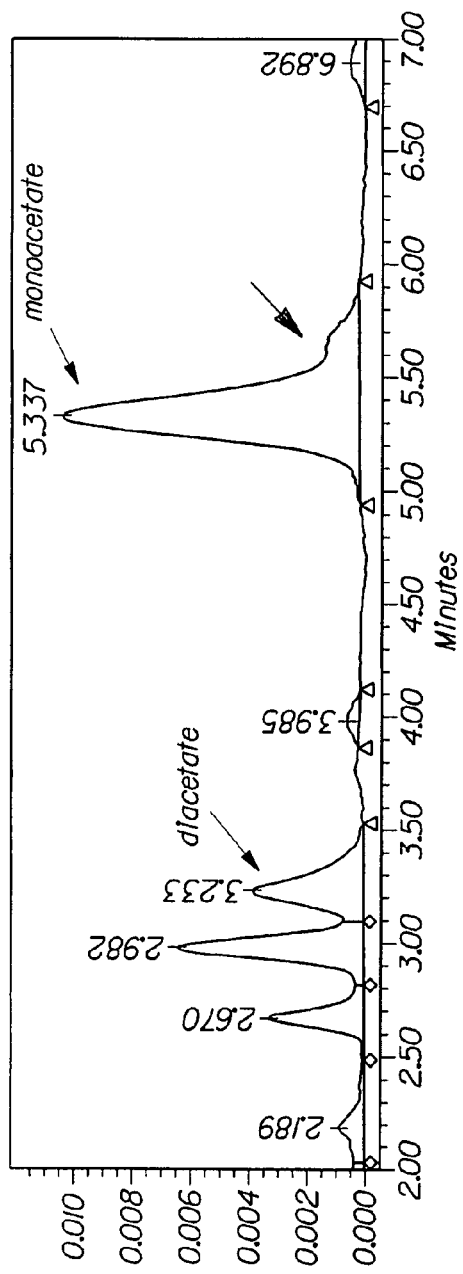
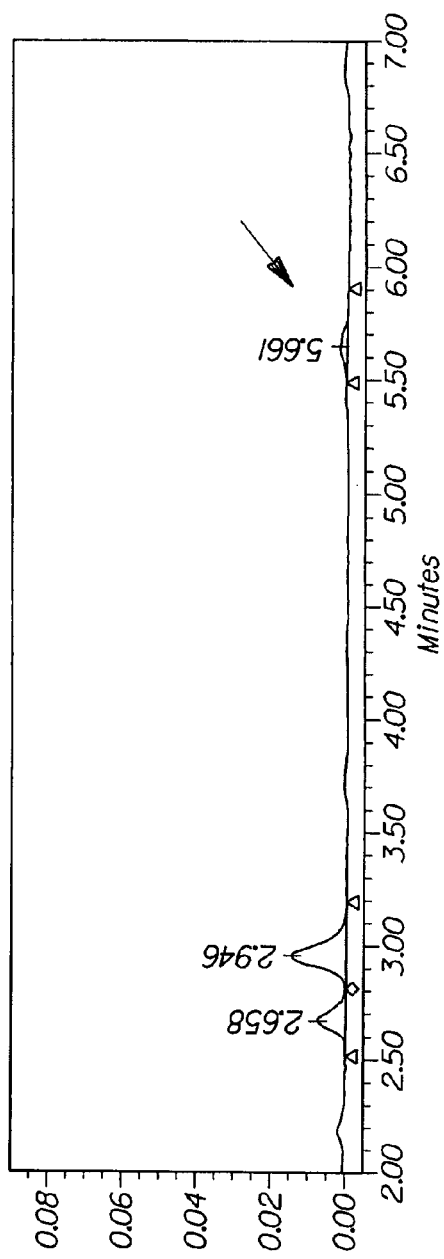
Fig. 1A
Fig. 1B

US 8,153,144 B2

STABLE MULTIPHASE COMPOSITION COMPRISING ALKYLAMPHOACETATE

CROSS REFERENCE TO RELATED APPLICATION

This application claims the benefit of U.S. Provisional Application No. 60/777,643 filed Feb. 28, 2006.

FIELD OF THE INVENTION

The present invention relates to a structured personal care composition comprising alkylamphoacetate.

BACKGROUND OF THE INVENTION

Personal cleansing compositions that attempt to provide skin-conditioning benefits are known. Desirable personal cleansing compositions must meet a number of criteria. For example, in order to be acceptable to consumers, a multiphase personal cleansing composition must exhibit good cleaning properties, must exhibit good lathering characteristics, must be mild to the skin (not cause drying or irritation) and preferably should even provide a conditioning benefit to the skin.

Many personal cleansing compositions are aqueous systems comprising an emulsified conditioning oil or other similar materials in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these cleansing and conditioning products. Raising the level of skin conditioning agent in order to achieve increased deposition may negatively affect the composition's speed of lather generation, total lather volume, performance and stability.

Alkylamphoacetates, such as sodium lauroamphoacetate, are typically used in personal cleansing compositions for improved product mildness and lather, and to improve structure and stability of the compositions. However, alkylamphoacetates can have impurities or unintended reaction products, such as alkylamphodiacetate. It is believed that maintaining acceptable stability, structure, lather and rheology in multiphase, personal care compositions has been a challenge due to the presence of impurities in alkylamphoaetates.

Accordingly, the need still remains for stable body wash composition comprising an alkylamphoacetate that provides cleansing with improved lathering characteristics, and which has improved structure, stability and rheology and skin benefits such as silky skin feel.

SUMMARY OF THE INVENTION

The multiphase personal care composition of the present invention comprises a first phase and a second phase. The first phase is comprised of structured surfactant phase that comprises at least about 0.5% of alkylamphoacetate. The alkylamphoacetate comprises a Percentage Diacetate of less than about 15%. In another embodiment, the multiphase personal care composition of the present invention comprises a first phase and a second phase; the first phase comprising a structured surfactant phase that comprises at least about 0.5% of sodium lauroamphoacetate. The sodium lauroamphoacetate comprises a Percentage Diacetate of less than about 15%. The composition of the present invention comprises an alkylamphoacetate comprising a low level of diacetate which maintains acceptable structure, stability and rheology with increased lather longevity and skin benefits in a multiphase personal care composition.

BRIEF DESCRIPTION OF THE DRAWINGS

FIG. 1(A) is a chromatogram of finished product in which the monoacetate peak of sodium lauroamphoacetate has significant tailing (arrow).

FIG. 1(B) is a chromatogram of a placebo finished product that confirms a matrix adduct co elutes as the source of tailing in the finished product (arrow).

DETAILED DESCRIPTION OF THE INVENTION

Figure 2A:
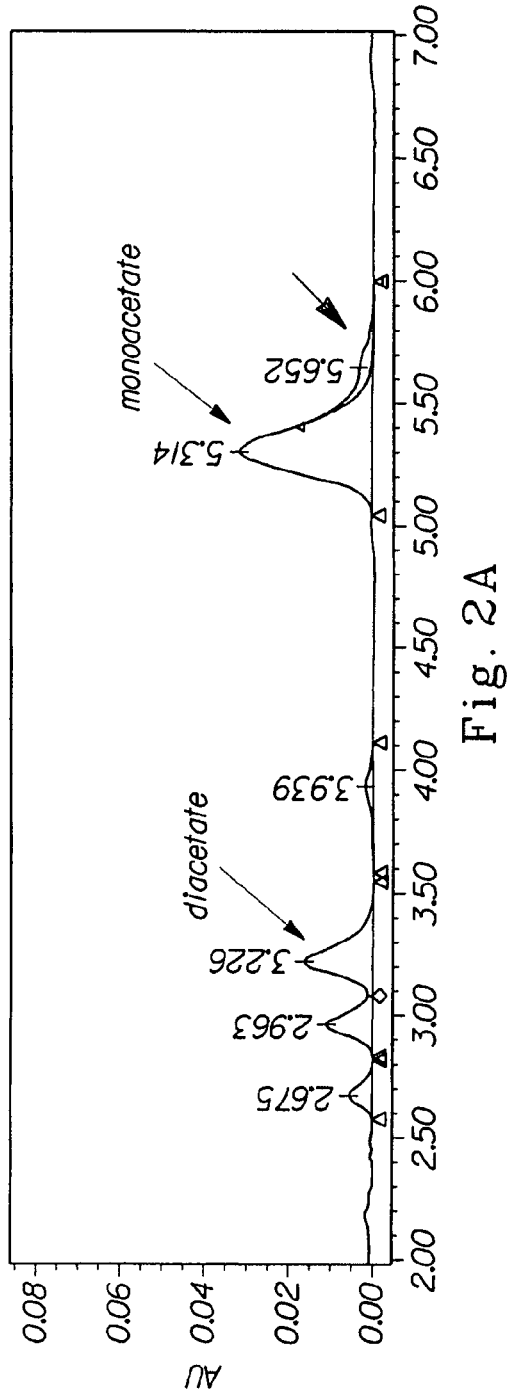
FIG. 2(A) is a chromatogram of finished product in which the monoacetate peak area has been corrected from matrix co-elution for integration using the Gaussian Skim feature in EMPOWER® Chromatography Software.

By the term "multiphase" or "multi-phase" as used herein, is meant that the phases of the present compositions occupy separate but distinct physical spaces inside the package in which they are stored, but are in direct contact with one another (i.e., they are not separated by a barrier and they are not emulsified or mixed to any significant degree). In one preferred embodiment of the present invention, the "multiphase" personal care compositions comprise at least two visually distinct phases which are present within the container as a visually distinct pattern. The pattern results from the combination of the "multi-phase" composition by a method of manufacture herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof.

In a preferred embodiment, the striped pattern can be relatively uniform across the dimension of the package. Alternatively, the striped pattern can be uneven, i.e. wavy, or can be non-uniform in dimension. The striped pattern does not need to necessarily extend across the entire dimension of the package. The size of the stripes can be at least about 0.1 mm in width and 10 mm in length, preferably at least about 1 mm in width and at least 20 mm in length as measured from the package exterior. The phases can be various different colors, and/or include particles, glitter or pearlescent agents in at least one of the phases in order to offset its appearance from the other phase(s) present.

The term "personal care composition" as used herein, refers to compositions intended for topical application to the skin and hair.

The term "structured," as used herein means having a rheology that confers stability on the multi-phase composition. The degree of structure is determined by characteristics determined by one or more of the following methods the Yield Stress Method, or the Zero Shear Viscosity Method or by the Ultracentrifugation Method, all in the Test Methods below. Accordingly, a surfactant phase of the multiphase composition of the present invention is considered "structured," if the surfactant phase has one or more of the following properties described below according to the Yield Stress Method, or the Zero Shear Viscosity Method or by the Ultracentrifugation Method. A surfactant phase is considered to be structured, if the phase has one or more of the following characteristics:

A. a Yield Stress of greater than about 0.1 Pascal (Pa), more preferably greater than about 0.5 Pa, even more preferably greater than about 1.0 Pa, still more preferably greater than about 2.0 Pa, still even more preferably greater than about 3 Pa, and even still even more preferably greater than about 5 Pa as measured by the Yield Stress and Zero Shear Viscosity Method described hereafter:

B. a Zero Shear Viscosity of at least about 500 Pascal-seconds (Pa-s), preferably at least about 1,000 Pa-s, more preferably at least about 1,500 Pa-s, even more preferably at least about 2,000 Pa-s; or C. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%.

The phrase "substantially free of" as used herein, unless otherwise specified means that the composition comprises less than about 5%, preferably less than about 3%, more preferably less than about 1% and most preferably less than about 0.1% of the stated ingredient.

The term "visually distinct phase" as used herein, refers to a region of the multiphase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase can also be constituted or re-constituted, collected, or separated into a bulk phase in order to observe its properties, e.g., by centrifugation, filtration or the like.

The multiphase, personal care composition of the present invention comprises a first phase and a second phase. The first phase comprises a structured surfactant phase that comprises at least about 0.5% alkylamphoacetate. The second phase of the multiphase personal care composition of the present invention can also comprise a benefit phase or a structured aqueous phase.

The structured surfactant phase may comprise from about 0.5% to about 20%, by weight of the multiphase personal care composition, of alkylamphoacetate. The structured surfactant phase may comprise from about 1.0% to about 5%, preferably from about 2.0% to about 5%, more preferably from about 1% to about 3%, by weight of the multiphase personal care composition, alkylamphoacetate. The percentage of alkylamphoacetate, in the multiphase personal care composition is determined by any conventional means known in the art, for example by formula weight.

Alkylamphoacetates are surfactants used in personal cleansing compositions for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Thus, the alkylamphoacetate of the present invention comprises a Percentage Diacetate of less than about 15%. Percentage Diacetate is described in the Reverse Phase HPLC Methods in the test below. The alkylamphoacetate of the present invention can comprises a Percentage Diacetate of less than about 10%, preferably a Percentage Diacetate of less than about 7%, more preferably a Percentage Diacetate of less than about 5%, and most preferably a Percentage Diacetate of less than about 3%.

The presence of diacetate tends to cause a decrease in stability in the presence of lipophilic conditioning agents. Moreover, the presence of diacetate in the alkylamphoacetate decreases the lather of the composition. Further, the monoacetate has a smaller head group size than diacetate, therefore, compositions that comprise monoacetate and little to no diacetate tends to interact better with neighboring surfactants, resulting in a personal care composition with better structure and rheology than those that have a higher amount of diacetate.

In some embodiments, the alkylamphoacetate is sodium lauroamphoacetate. Sodium lauroamphoacetate can be a relatively pure molecule, such as 80% or more $C_{12}$, or a mixture of several molecules where $C_{12}$ is a dominant hydrocarbon moiety, such as sodium lauroamphoacetate derived from coconut oil. It can be derived from fats and oils, petroleum or via the Fisher Tropsch gas to liquid process. One common derivative could be from natural sources such as coconut or palm kernel oil, followed by subsequent fractionation. Sodium alkylamphoacetate or sodium lauroamphoacetate could have a carbon chain length distribution where 90% of the chain lengths are $C_{10}$ to $C_{18}$. Another typical chain length distribution would include 45% to 70% of the chain length $C_{12}$. The carbon backbone can be linear or branched. These and many other possibilities would be obvious to those knowledgeable in the relevant art. Additionally, there may be a mixture of monoacetates or diacetates.

The multiphase personal care composition of the present invention is typically extrudable or dispensible from a package. The multiphase personal care compositions typically exhibit a viscosity of from about 1,500 centipoise (cP) to about 1,000,000 cP, as measured by the Viscosity Method as described in the published U.S. Application No. 2004/0223991A1 entitled "Multi-phase Personal Care Compositions."

When evaluating a structured multiphase personal care composition, by the methods described herein, preferably each individual phase is evaluated prior to combining, unless otherwise indicated in the individual methodology. However, if the phases are combined, each phase can be separated by centrifugation, pipetting, filtering, washing, dilution, concentration, or combination thereof, and then the separate phase or phases can be evaluated. Preferably, the separation means is chosen so that the resulting separated components being evaluated is not destroyed, but is representative of the component as it exists in the structured multiphase personal care composition, i.e., its composition and distribution of components therein is not substantially altered by the separation means. Generally, multiphase compositions comprise domains significantly larger than colloidal dimensions so that separation of the phases into the bulk is relatively easy to accomplish while retaining the colloidal or microscopic distribution of components therein. Preferably, the compositions of the present invention are rinse-off formulations, by which is meant the product is applied topically to the skin or hair and then subsequently the skin or hair is rinsed with water.

In a preferred embodiment of the present invention, the multiphase personal care composition comprises at least two visually distinct phases wherein a first phase is visually distinct from a second phase. Preferably, the visually distinct phases are packaged in physical contact with one another and are stable. Preferably, the visually distinct phases form a pattern.

Phases: The multiphase personal care compositions of the present invention comprise at least two visually distinct phases, wherein the composition can have a first structured phase, a second phase, a third phase, a fourth phase and so on. The ratio of a first phase to a second phase is preferably from about 99:1 to about 1:99, preferably from about, 90:10 to about 10:90, more preferably from about 80:20 to about 20:80, even more preferably from about 70:30 to about 30:70.

Structured Surfactant phase: The first phase of the multiphase personal care composition of the present invention comprises a structured surfactant phase. Moreover, the second phase of the multiphase personal care composition of the present invention can comprise a structured surfactant phase. The surfactant phase preferably comprises a lathering surfactant or a mixture of lathering surfactants. The surfactant phase comprises surfactants suitable for application to the skin or hair. Suitable surfactants for use herein include any known or otherwise effective surfactant suitable for application to the skin, and which are otherwise compatible with the other essential ingredients in the multiphase personal care composition including water. These surfactants include anionic, nonionic, cationic, zwitterionic, amphoteric surfactants, soap, or combinations thereof. Preferably, anionic surfactant comprises at least 40% of the surfactant phase.

The multiphase personal care composition preferably comprises surfactants at concentrations ranging from about 2% to about 70%, more preferably from about 4% to about 40%, even more preferably from about 6% to about 30% by weight of the structured surfactant phase.

The surfactant phase is preferably comprised of a structured domain comprising surfactants. The structured domain enables the incorporation of high levels of benefit components in a separate phase that are not emulsified in the composition. In a preferred embodiment the structured domain is an opaque structured domain. The opaque structured domain is preferably a lamellar phase. The lamellar phase produces a lamellar gel network. The lamellar phase can provide resistance to shear, adequate yield to suspend particles and droplets and at the same time provides long term stability, since it is thermodynamically stable. The lamellar phase tends to have a viscosity that minimizes the need for viscosity modifiers.

Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al on Dec. 30, 1975.

Preferred linear anionic surfactants for use in the structured surfactant phase of the multiphase, personal care composition include ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and combinations thereof.

Branched anionic surfactants and monomethyl branched anionic surfactants suitable for the present invention are described in commonly owned U.S. Application Ser. No. 60/680,149 entitled "Structured Multi-phased Personal Cleansing Compositions Comprising Branched Anionic Surfactants" filed on May 12, 2005 by Smith, et al. Branched anionic surfactants include but are not limited to the following surfactants: sodium trideceth sulfate, sodium tridecyl sulfate, sodium $C_{12-13}$ alkyl sulfate, and $C_{12-13}$ pareth sulfate and sodium $C_{12-13}$ pareth-n sulfate.

In addition to the alkylamphoacetates, other amphoteric surfactants are suitable for use in the multiphase composition of the present invention. The amphoteric surfactants include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, and N-alkyltaurines. Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase, personal care composition include betaines, including cocoamidopropyl betaine.

Non-limiting examples of preferred nonionic surfactants for use herein are those selected form the group consisting of glucose amides, alkyl polyglucosides, sucrose cocoate, sucrose laurate, alkanolamides, ethoxylated alcohols and mixtures thereof. In a preferred embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Mixtures of anionic surfactants can be used in some embodiments, including mixtures of linear and branched surfactants, and anionic surfactants combined with nonionic, amphoteric, and/or zwitterionic surfactants.

An electrolyte, if used, can be added per se to the multiphase personal care composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate. The electrolyte is preferably added to the structured surfactant phase of the composition in the amount of from about 0.1% to about 15% by weight, preferably from about 1% to about 6% by weight, more preferably from about 3% to about 6%, by weight of the structured surfactant composition.

In one embodiment of the present invention, the multiphase, personal care composition comprises a structured surfactant phase comprising a mixture of at least one nonionic surfactant, and an electrolyte. In another embodiment, the surfactant phase can comprise a mixture of surfactants, water, at least one anionic surfactant, an electrolyte, and at least one alkanolamide.

Benefit Phase: The second phase of multiphase personal care compositions of the present invention can comprise a benefit phase. The benefit phase in the present invention is preferably anhydrous and can be substantially free of water. The benefit phase can comprise less than about 5% water, preferable less than 3% water or most preferably less than 1% water. The benefit phase can be substantially free of surfactant. The benefit phase can comprise less than about 5% of surfactant, more preferably less than about 3% of surfactant and most preferably less than about 1% surfactant.

The benefit phase typically comprises hydrophobic moisturizing materials. The benefit phase can be comprised of the components selected from the group consisting of petrolatum, lanolin, hydrocarbon oils such as mineral oil, natural and synthetic waxes such as micro-crystalline waxes, paraffins, ozokerite, lanolin wax, lanolin alcohols, lanolin fatty acids, polyethylene, polybutene, polydecene and perhydrosqualene, volatile or non-volatile organosiloxanes and their derivatives such as dimethicones, cyclomethicones, alkyl siloxanes, polymethylsiloxanes and methylphenylpolysiloxanes, lanolin oil, esters such as isopropyl lanolate, acetylated lanolin, acetylated lanolin alcohols, lanolin alcohol linoleate, lanolin alcohol riconoleate natural and synthetic triglycerides such as castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, and combinations thereof.

The benefit phase may comprise from about 1% to about 100%, preferably at least about 15%, preferably at least about 17.5%, preferably at least about 20%, preferably at least about 24%, preferably at least about 30%, by weight of the benefit phase, of a hydrophobic moisturizing material. Hydrophobic moisturizing materials suitable for use in the present invention preferably have a Vaughan Solubility Parameter of from about 5 $(cal/cm^3)^{1/2}$ to about 15 $(cal/cm^3)^{1/2}$, as defined by *Vaughan in Cosmetics and Toiletries*, Vol. 103. Non-limiting examples of hydrophobic moisturizing materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product Package, Penetration and Preservation*, C. D. Vaughan, Cosmetics and Toiletries, Vol. 103, October 1988.

The hydrophobic materials are preferably selected among those having defined Theological properties as described hereinafter, including selected Consistency value (K) and Shear Index (n). These preferred Theological properties are especially useful in providing the personal care compositions with lubrication of the skin surface for shaving and for improved deposition of hydrophobic moisturizing materials. The benefit phase has a Consistency Value (K) from about 20 to about 2,000 Pa-s, preferably from about 25 to about 500 Pa-s, more preferably from about 30 to about 450 Pa-s, still more preferably from about 30 to about 400 Pa-s and even still more preferably from about 30 to about 350 Pa-s. The benefit phase has a Shear Index from about 0.025 to about 0.99.

Examples of suitable benefit phases and description of measuring the values of Consistency (K) and Shear Index (n) are described in U.S. patent application Ser. No. 10/665,670, Publication No. 2004/0057920 A1 entitled Striped liquid personal cleansing compositions containing a cleansing phase and a separate benefit phase" filed by Fact, et al. on Sep. 18, 2003, published on Apr. 4, 2004, U.S. patent application Ser. No. 10/699,469 Publication No. 2004/0092415 A1 entitled "Striped liquid personal cleansing compositions containing a cleansing phase and a separate benefit phase with improved stability" filed by Fact, et al. on Oct. 31, 2003, published on May 13, 2004 and U.S. patent application Ser. No. 10/837,214 Publication No. 2004/0219119 A1 entitled "Visually distinctive multiple liquid phase compositions" filed by Weir, et al. on Apr. 30, 2004, published on Nov. 18, 2004.

Structured Aqueous Phase: The second phase of the multiphase personal care compositions of the present invention can comprise a structured aqueous phase that comprises a water structurant and water. The structured aqueous phase can be hydrophilic and in a preferred embodiment the structured aqueous phase is a hydrophilic, non-lathering gelled water phase. In addition, the structured aqueous phase typically comprises less than about 5%, preferably less than about 3%, and more preferably less than about 1%, by weight of the structured aqueous phase, of a surfactant. In one embodiment of the present invention, the structured aqueous phase is free of lathering surfactant in the formulation. A preferred structured aqueous phase is a non-lathering structured aqueous phase as described in published U.S. Patent Application No. 2005/0143269A1 entitled "Multi-phase Personal Cleansing Compositions Containing A Lathering Cleansing Phase And A Non-Lathering Structured Aqueous Phase."

The structured aqueous phase of the present invention can comprise from about 30% to about 99%, by weight of the structured aqueous phase, of water. The structured aqueous phase generally comprises more than about 50%, preferably more than about 60%, even more preferably more than about 70%, and still more preferably more than about 80%, by weight of the structured aqueous phase, of water.

The structured aqueous phase will typically have a pH of from about 5 to about 9.5, more preferably about 7. A water structurant for the structured aqueous phase can have a net cationic charge, net anionic charge, or neutral charge. The structured aqueous phase of the present compositions can further comprise optional ingredients such as, pigments, pH regulators (e.g. triethanolamine), and preservatives.

The structured aqueous phase can comprise from about 0.1% to about 30%, preferably from about 0.5% to about 20%, more preferably from about 0.5% to about 10%, and even more preferably from about 0.5% to about 5%, by weight of the structured aqueous phase, of a water structurant.

The water structurant is typically selected from the group consisting of inorganic water structurants, charged polymeric water structurants, water soluble polymeric structurants, associative water structurants, and mixtures thereof. Non-limiting examples of inorganic water structurants include silicas, polymeric gellants such as polyacrylates, polyacrylamides, starches, modified starches, crosslinked polymeric gellants, copolymers, and mixtures thereof. Non-limiting examples of charged polymeric water structurants for use in the multi-phase personal care composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers, Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), and mixtures thereof. Non-limiting examples of water soluble polymeric structurants for use in the multi-phase personal care composition include cellulose gums and gel, and starches. Non-limiting examples of associative water structurants for use in the multi-phase personal care composition include xanthum gum, gellum gum, pectins, alginates such as propylene glycol alginate, and mixtures thereof.

Density Modifiers: To further improve stability under stressful conditions such as high temperature and vibration, it is preferable to adjust the densities of the separate phases such that they are substantially equal. To achieve this, low density microspheres can be added to one or more phases phase of the personal care composition, preferably the structured surfactant phase. The low density microspheres employed to reduce the overall density of the structured surfactant phase are particles having a density lower than 0.7 g/cm$^3$, preferably less than 0.2 g/cm$^3$. The low density microspheres generally have an average diameter less than 200 µm, preferably less than 100 µm. When the composition comprises phases which are visually distinct from each other, preferably, the density difference between the structured surfactant phase and the benefit phase is less than 0.15 g/cm$^3$, more preferably, the density difference is less than 0.10 g/cm$^3$, even more preferably, the density difference is less than 0.05g/cm$^3$. The microspheres are produced from any appropriate inorganic or organic material, compatible with a use on the skin, that is, nonirritating and nontoxic.

Expanded microspheres are known, and may be obtained, for example, according to the processes described in Patents and Patent Applications EP-56219, EP-348372, EP-486080, EP-320473, EP-112807 and U.S. Pat. No. 3,615,972.

These microspheres may be produced from any nontoxic and non-irritant thermoplastic materials. These microspheres can be in the dry or hydrated state. Among hollow microspheres which can be used, special mention may be made of those marketed under the brand name EXPANCEL® (thermoplastic expandable microspheres) by the Akzo Nobel Company, especially those of DE (dry state) or WE (hydrated state) grade. Representative microspheres derived from an inorganic material, include, for instance, "QCEL® Hollow Microspheres" and "EXTENDOSPHERES"™ Ceramic Hollow Spheres", both available from the PQ Corporation.

The phases of the multiphase personal care composition, preferably the structured surfactant phase, can further comprise a polymeric phase structurant. The compositions of the present invention typically can comprise from about 0.05% to about 10%, preferably from about 0.1% to about 4%, of a polymeric phase structurant. Non-limiting examples of polymeric phase structurant include but are not limited to the following examples: naturally derived polymers, synthetic polymers, crosslinked polymers, block copolymers, copolymers, hydrophilic polymers, nonionic polymers, anionic polymers, hydrophobic polymers, hydrophobically modified polymers, associative polymers, and oligomers.

The phases of the present compositions, preferably the structured surfactant phase, optionally can further comprise a liquid crystalline phase inducing structurant, which when present is at concentrations ranging from about 0.3% to about 15%, by weight of the phase. Suitable liquid crystalline phase inducing structurants include fatty acids (e.g. lauric acid, oleic acid, isostearic acid, linoleic acid) ester derivatives of fatty acids (e.g. propylene glycol isostearate, propylene glycol oleate, glyceryl isostearate) fatty alcohols, trihydroxystearin (available from Rheox, Inc. under the trade name THIXCIN® R). Preferably, the liquid crystalline phase inducing structurant is selected from lauric acid, trihydroxystearin, lauryl pyrrolidone, and tridecanol.

The multiphase personal care compositions of the present invention can additionally comprise an organic cationic deposition polymer in the one or more phases as a deposition aid for the benefit agents described herein. Suitable cationic deposition polymers for use in the compositions of the present invention contain cationic nitrogen-containing moieties such as quaternary ammonium moieties.

One or more of the phases of the multiphase personal care composition can comprise a variety of additional optional ingredients such as shiny particles, beads, exfoliating beads. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Other non limiting examples of these optional ingredients include vitamins and derivatives thereof (e.g., ascorbic acid, vitamin E, tocopheryl acetate, and the like), sunscreens; thickening agents, preservatives for maintaining the anti microbial integrity of the cleansing compositions, anti-acne medicaments, antioxidants, skin soothing and healing agents such as aloe vera extract, allantoin and the like, chelators and sequestrants, skin lightening agents, and agents suitable for aesthetic purposes such as fragrances, essential oils, skin sensates, pigments, pearlescent agents and essential oils and fragrance.

TEST METHODS

Ultracentrifugation Method: The Ultracentrifugation Method is used to determine the percent of a structured domain or an opaque structured domain that is present in a multi-phase personal care composition that comprises a structured surfactant phase comprising a surfactant component. The method involves the separation of the composition by ultracentrifugation into separate but distinguishable layers. The multi-phase personal care composition of the present invention can have multiple distinguishable layers, for example a non-structured surfactant layer, a structured surfactant layer, and a benefit layer.

First, dispense about 4 grams of multi-phase personal care composition into Beckman Centrifuge Tube (11×60 mm). Next, place the centrifuge tubes in an Ultracentrifuge (Beckman Model L8-M or equivalent) and ultracentrifuge using the following conditions: 50,000 rpm, 18 hours, and 25° C.

After ultracentrifuging for 18 hours, determine the relative phase volume by measuring the height of each layer visually using an Electronic Digital Caliper (within 0.01 mm). First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation:

$$H_s = H_a - H_b$$

The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure. There may be several structured layers present, so that $H_c$ is the sum of the individual structured layers. If a coacervate phase or any type of polymer-surfactant phase is present, it is considered a structured phase.

Finally, the structured domain volume ratio is calculated as follows:

Structured Domain Volume Ratio=$H_c/H_s*100\%$

If there is no benefit phase present, use the total height as the surfactant layer height, $H_s = H_a$.

Yield Stress and Zero Shear Viscosity Method: The Yield Stress and Zero Shear Viscosity of a phase of the present composition, can be measured either prior to combining in the composition, or after combining in the composition by separating the phase by suitable physical separation means, such as centrifugation, pipetting, cutting away mechanically, rinsing, filtering, or other separation means.

A controlled stress rheometer such as a TA Instruments AR2000 Rheometer is used to determine the Yield Stress and Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress. Serrated plates can be used to obtain consistent results when slip occurs.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 4 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

Log(strain)=$m$*Log(stress)+$b$ (1)

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

% variation=100*(measured strain−predicted strain)/measured strain (2)

The Yield Stress is the first stress (Pa) at which % variation exceeds 10% and subsequent (higher) stresses result in even greater variation than 10% due to the onset of flow or deformation of the structure. The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

The Shear Index (n) and Consistency Value (K): The Shear Index (n) and Consistency Value (K) are known and accepted means for reporting the viscosity profile of materials having a viscosity that varies with applied shear rate using a Power Law model. The term "Consistency value" or "K" as used herein is a measure of viscosity and is used in combination with Shear Index, to define viscosity for materials whose viscosity is a function of shear rate. The measurements of Consistency value and Shear Index are made at 25° C. The units for "Consistency value" or "K" are Pascal seconds. The units for "Shear Index" are dimensionless.

Viscosity of a phase can be measured by applying a shear stress and measuring the shear rate using a rheometer, such as a TA Instruments AR2000 (TA Instruments, New Castle, Del., USA 19720). Viscosity is determined at different shear rates in the following manner. First, the benefit phase is obtained. If there exists more than one distinct (immiscible, e.g.) benefit phase in the composition, such as for example a silicone oil phase and a hydrocarbon phase, they are preferably prepared separately and/or separated from each other, and evaluated separately from each other, although certain benefit phases which are mixtures such as emulsions can be evaluated as mixtures, in addition to evaluating the individual benefit phases individually.

For measurement, a 40 mm diameter parallel plate geometry with a gap of 1 mm is used unless there are particles greater than 0.25 mm, in which case a gap of 2 mm is used. The rheometer uses standard parallel plate conventions to report shear rate at the edge as shear rate of the test; and converts torque to stress using the factor $2/(\pi R^3)$. Using a spatula, a sample comprising a small excess of the benefit phase is loaded onto the rheometer base plate which is at 25° C., the gap is obtained, and excess composition outside the top measurement geometry is removed, locking the top plate in position during the removal of excess sample. The sample is equilibrated to the base plate temperature for 2 minutes. A preshear step is performed comprising 15 seconds of shear at a shear rate of 50 inverse seconds (1/sec). As is known to one skilled in the art, the shear rate with a parallel plate geometry is expressed as the shear rate at the edge, which is also the maximum shear rate. After the preshear step, the measurement is performed, which comprises ramping the stress from 10 Pa to 1,000 Pa over a 2.0 minute interval at 25° C., while collecting 60 viscosity data points, in an evenly spaced linear progression. A shear rate of at least 500 1/seconds is obtained in the test, or the test is repeated with a fresh sample of the same component with a higher final stress value, maintaining the same rate of stress increase per time, until a shear rate of at least 500 1/sec is obtained during the measurement period. During the measurement, observe the sample to make certain the area under the top parallel plate is not evacuated of sample at any edge location during the measurement, or the measurement is repeated until a sample remains for the duration of the test. If after several trials a result cannot be obtained due to sample evacuation at the edge, the measurement is repeated leaving an excess reservoir of material at the edge (not scraping). If evacuation still cannot be avoided, a concentric cylinder geometry is used with a large excess of sample to avoid air pockets during loading. The results are fitted to the power law model by selecting only the data points between 25-500 1/sec shear rate, viscosity in Pa-s, shear rate in 1/sec, and using a least squares regression of the logarithm of viscosity vs. the logarithm of shear rate to obtain values of K and n according to the Power Law equation:

$$\mu = K(\gamma')^{(n-1)}$$

The value obtained for the log-log slope is (n−1) where n is the Shear Index and the value obtained for K is the Consistency Value, expressed in units of in Pa-s.

Density (Specific Gravity) Method:

The metal pycnometer is utilized for determination of density (specific gravity) of both the structured surfactant phase and the benefit phase compositions. One suggested type of metal pycnometer can be obtained from Fisher, 3-347. Other equivalent pycnometers can also be used. To measure the density (specific gravity) the following procedure is used.

The first step is cleaning. The metal pycnometer must be clean and dry before use. Diassemble the metal pycnometer completely and wash all parts well with water. Follow the water rinse with an alcohol rinse. Expel the alcohol with a stream of dry, clean air.

The second step is standardization. Fill the clean, dry pycnometer with distilled water at 25° C. Place the lid on body of pycnometer and screw the cap firmly in place. Dry the outside of pycnometer well with a tissue and weigh to 0.001 g. Clean and dry the pycnometer according to the directions shown above. Assemble and weigh the dry pycnometer to 0.001 g.

Water weight=Weight of pycnometer and water−weight of empty pycnometer

The third step is sample measurement. Clean and dry the pycnometer according to the directions shown above. Allow the sample to equilibrate to room temperature. Pour the sample into the pycnometer, taking care to avoid introducing air into the sample in the pycnometer. Add an excess of sample so that it extends slightly above the top of the threads. Place the lid inside the cap and screw the cap firmly onto the body of the pycnometer. Any excess sample will be forced through the hole in the lid of the pycnometer. Wipe away the excess sample carefully with a tissue. Weight the filled pycnometer to 0.001 g.

Sample Weight=Weight of pycnometer and sample−weight of pycnometer.

The forth step is specific gravity. Specific Gravity=Weight of Sample/Weight of Water.

The density difference between the structured surfactant phase and the benefit phase is less than 0.15 g/cm³, preferably, the density difference is less than 0.10 g/cm³, more preferably, the density difference is less than 0.05 g/cm³.

Reverse Phase HPLC Method: Reverse Phase HPLC can determine the percentage of diacetate in an alkylamphoacetate or in a personal care composition comprising an alkylamphoacetate or in a raw chemical component. Reverse Phase HPLC can determine the monoacetate to diacetate ratio of alkylamphoacetate in a personal care composition or in a raw chemical component. The ratio is based on the peak areas obtained for monoacetate and diacetate when tested by the chromatographic conditions outlined below. A placebo can be tested to correct for interference of matrix components/adducts which may co-elute or contribute to the monoacetate and diacetate peak areas.

First a Mobile Phase is prepared by the following steps:. Weigh 4.5±0.1 g $NaH_2PO_4$ into a 4 L beaker. Dissolve by stirring in 1000 ml of purified water. Using phosphoric acid adjust pH to 2.5'/−0.01 by drop addition. Add 2 L of methanol (final pH will be around 4). Degas under vacuum for 10 minutes. Allow to equilibrate to room temperature before use.

Next, add 30 ml of Mobile Phase to a 50 ml volumetric flask. Weigh 0.15+/−0.01 g of a personal care composition into the flask and disperse by shaking, then sonicating for up to 60 minutes. Bring to volume (50 ml) with additional Mobile Phase. After thoroughly mixing, filter into an auto sample vial for injection into the HPLC. To evaluate monoacetate and diacetate in for a raw chemical component such as a surfactant or a mixture of surfactants, first add about 60 ml of Mobile Phase into a 100 ml volumetric flask, then weigh in 0.20+/−0.01 g of sample directly avoiding transfer to the neck. Disperse and bring to volume (100 ml) with additional Mobile Phase Pipette 3.0 ml into a 10 ml volumetric flask, bring to volume (10 ml) with additional Mobile Phase. Thoroughly mix, filter into an auto sample vial for injection into the HPLC. When the raw chemical component is known to contain primarily an alkylamphoacetate comprising monoacetate and diacetate, this can be used as a reference/standard to verify retention times of the mono and diacetate peaks of alkylamphoacetate in the finished product.

| EQUIPMENT | |
| --- | --- |
| HPLC Pump | Waters, Model 600 or equivalent |
| HPLC Autosampler | Waters, Model 717 or equivalent |
| HPLC PDA | Waters, Model 996 or equivalent |
| Data System | Waters, Millennium 32 Chromatography Manager or equivalent |
| HPLC Vial | Waters, 2 mL, glass, cat# WAT073018 or equivalent |
| Column | Waters Novapack C18 3.9 × 150 mm Cat # WAT086344 (no substitution allowed) |
| Analytical balance | Capable of weighing to 0.0001 g |
| pH meter | Capable of measuring 0.01 pH units |
| Sonication Bath | Branson 5200 or equivalent |
| Glassware | General class A glassware |
| 0.45 Micron PTFE acrodisc | Gelman or equivalent |
| 0.45 Micron membrane HA | Millipore or equivalent |

| REAGENTS AND SOLUTIONS | GRADE & TYPICAL SOURCE |
| --- | --- |
| Sodium dihydrogen phosphate monohydrate $NaH2PO4 \cdot H2O$ | Merck purity >99% or equivalent |
| Purified Water | |
| Ortho Phosphoric acid H3PO4 | RDH purity 85% or equivalent |
| Methanol | Mallinckrodt HPLC grade or equivalent |

| PREPARATION OF HPLC EQUIPMENT SETTINGS | |
|---|---|
| Flow Rate | 1.5 mL/min (typical backpressure 3000 psi.) |
| Column Temperature | Room Temperature |
| Run Time | 15 min for standards, 35 minutes for samples. |
| Injection Volume | 20 μL |
| Detector Wavelength | 205 nm |

Retention times under these conditions are around 5 minutes for the mono-acetate peak and 3 minutes for the diacetate peak in raw materials. Sample chromatograms are shown in FIGS. 1 and 2.

System Suitability/Quality Control Requirements: Inject 100 μl of raw material reference STD solution to condition the column before analyzing samples. If stored unused for long periods or new, ensure proper conditioning of the column by injecting a raw material standard three times and calculating a relative percent standard deviation (% RSD) from the responses. A % RSD less than or equal to 3% is acceptable. If the % RSD is greater than 3, inject 100 ul of the stock raw material STD again, and repeat the % RSD determination.

Calculation: Peak area is calculated using peak integration software (WATERS® EMPOWER™ Chromatography Software, Waters Corp., USA, 508-482-2614, or equivalent). Care is given to avoid integration of adducts or interference from matrix components which can artificially contribute to the peaks. A placebo can be run to account for adducts or interference of matrix components which may then be back subtracted to a best Gaussian fit (using the Gaussian skim feature in Empower) to determine the ratio. Examples of how this integration is done are illustrated herein below. Diacetate as a percentage of monoacetate is determined by taking the ratio of the calculated area under the respective peaks using the indicated software according to the following equation, and is expressed as Percentage Diacetate in the sodium lauroamphoacetate (NaLaa).

Percentage Diacetate=100×Diacetate Calc. Peak area/Monoacetate Calc. Peak area

FIG. 1(A) is a chromatogram of finished product in which the monoacetate peak has significant tailing (arrow). FIG. 1(B) is a Placebo chromatogram confirms a matrix adduct co elutes as the source of tailing in the finished product (arrow).

Figure 2B:
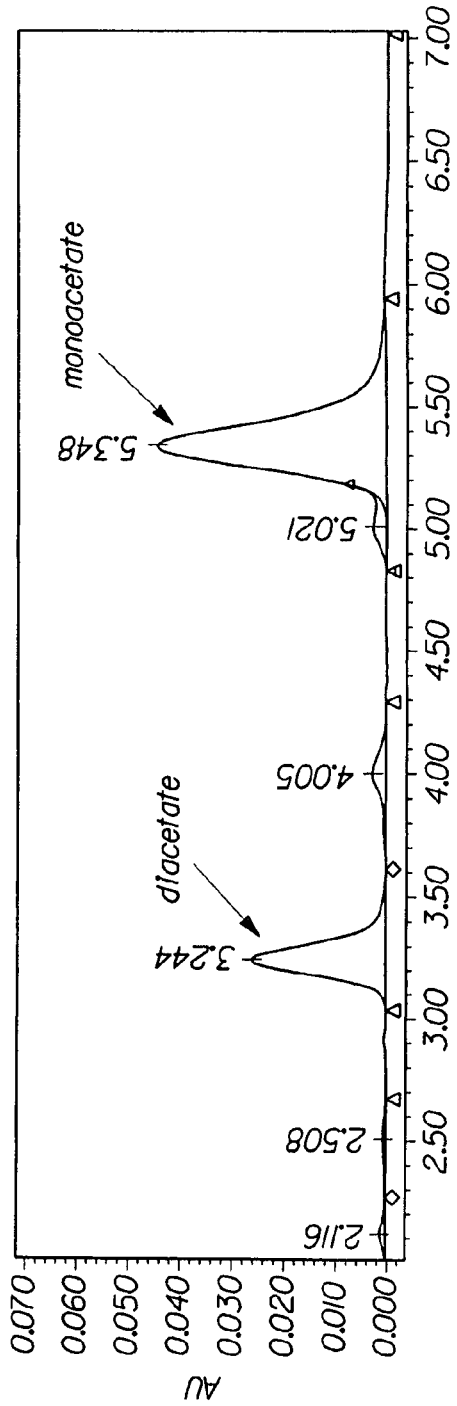
FIG. 2(B) is a reference raw material chromatogram of sodium lauroamphoacetate used in finished product confirms mono and diacetate peak retention times.

FIG. 2(A) is a chromatogram of finished product in which the monoacetate peak area has been corrected from matrix co-elution for integration using the Gaussian Skim feature in EMPOWER. FIG. 2(B) is a reference raw material chromatogram of NaLaa used in finished product confirms mono and diacetate peak retention times.

Ultracentrifugation "Third-Phase" Method for Determining Structured Surfactant Stability: The Ultracentrifugation "Third-Phase" Method is used to determine structured structured surfactant phase stability in a personal cleansing composition.

The method involves separation of the composition through ultracentrifugation into separate but distinguishable layers. The personal cleansing composition of the present invention can have multiple distinguishable layers, for example a non-structured surfactant layer, an opaque structured surfactant layer, a clear "third-phase" layer, and benefit phase layers.

The rapid stability aging protocol is set as follow. Prepare a lipid blend by heating a vessel to 180° F. (82.2° C.) and add Petrolatum (Quidesa Petrolatum from Quidesa, Mexico) and Hydrobrite 1000 White Mineral Oil (from WITCO, USA) at 65:35 weight ratio. Cool the vessel to 110° F. (43.3° C.) with slow agitation (200 rpm). Stop agitation and cool the vessel to ambient temperature overnight. Add 36 grams of lipid blend (65/35 Pet/MO) to about 44 grams of the structured surfactant composition. Mix the surfactant and lipid together using a spatula for 5 minutes. Place the mixed sample at 120° F. (48.9° C.) for 10 days. After rapid aging stability testing, transfer about 4 grams of the composition into a Beckman Centrifuge Tube (11×60 mm). Place the centrifuge tube in a Beckman LE-80 Ultracentrifuge and operate the Ultracentrifuge under the following conditions: 50,000 rpm, 2 hours, and at 40° C.

After Ultracentrifugation, determine the third-phase volume by measuring the height of various surfactant phases using an Electronic Digital Caliper (within 0.01 mm) as shown below. An example is shown below for a cleansing composition comprising Expancel microspheres, petrolatum, mineral oil and a structured surfactant phase.

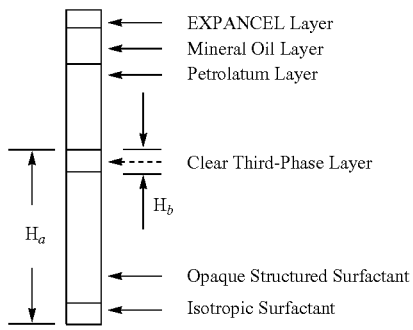

When a density modifier such as Epancel hollow microspheres is used, the very top layer primarily comprises the EXPANCEL microspheres. The second layer from the top is the clear mineral oil layer. The third layer from the top is the petrolatum layer. The layers below the petrolatum layers contain aqueous surfactant and are characterized as follows: $H_a$ is the height of all the aqueous and/or aqueous surfactant layers and $H_b$ is the height of the clear "third-phase" layer just below the petrolatum layer. It is important to record the readings within 30 minutes after the Ultracentrifugation is finished to minimize material migration. The third phase volume is calculated as: Third-phase Volume %=$H_b/H_a$*100%

Preferably, the structured surfactant composition comprises less than 5% "third-phase" volume after rapid aging protocol. More preferably, the structured surfactant composition comprises less than 2% "third-phase" volume after rapid aging protocol. Most preferably, the structured surfactant composition comprises less than 1% "third-phase" volume after rapid aging protocol.

METHOD OF USE

The personal care compositions of the present invention are preferably applied topically to the desired area of the skin or hair in an amount sufficient to provide effective delivery of the skin cleansing agent, hydrophobic material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water. The present invention is therefore also directed to methods of cleansing the skin through the above-described application of the compositions of the present invention.

METHODS OF MANUFACTURE

The multi-phase personal care compositions of the present invention may be prepared by any known or otherwise effective technique, suitable for making and formulating the desired multi-phase product form. It is also effective to combine toothpaste-tube filling technology with a spinning stage design. Additionally, the present invention can be prepared by the method and apparatus as disclosed in U.S. Pat. No. 6,213,166 issued to Thibiant, et al. on Apr. 10, 2001. The method and apparatus allows two or more compositions to be filled in a spiral configuration into a single container using at least two nozzles which fill the container, which is placed on a static mixer and spun as the composition is introduced into the container.

Alternatively, the present invention can be prepared by a method disclosed in commonly owned U.S. patent application Ser. No. 10/837,214 Publication No. 2004/0219119 A1 entitled "Visually distinctive multiple liquid phase compositions" filed by Wei, et al. on Apr. 30, 2004, published on Nov. 18, 2004. The method and apparatus allows two separate compositions to be combined in predetermined amounts, blended into a single resultant composition with visually distinct phases, and filled by one nozzle into a single container that is lowered and rotated during filling.

If the multi-phase personal care compositions are patterned, it can be desirable to be packaged as a personal care article. The personal care article would comprise these compositions in a transparent or translucent package such that the consumer can view the pattern through the package. Because of the viscosity of the subject compositions it may also be desirable to include instructions to the consumer to store the package upside down, on its cap to facilitate dispensing.

EXAMPLES

The following example described in Table 1 shows non-limiting examples of the multi-phase composition of the present invention and a comparative example.

TABLE 1

Examples of the Present Invention and Comparative Example

|  | Example A of the Present Invention | Example B of the Present Invention | Comparative Example |
|---|---|---|---|
| Structured Surfactant Phase Composition | | | |
| Sodium Lauroamphoacetate (Miranol L-32, Rhodia Inc.) | — | — | 4.6 |
| Sodium Lauroamphoacetate (Cognis Chemical Corp.,) | 4.8 | 4.6 | — |
| Sodium Trideceth Sulfate (sulfated from Iconol TDA-3 (BASF Corp.) to >95% sulfate) | 8.1 | 7.7 | 7.7 |
| Sodium Lauryl Sulfate | 8.1 | 7.7 | 7.7 |
| Trideceth-3 (Iconal TDA-3 from BASF Corp.) | 2 | — | — |
| Isosteareth-2 (Global Seven, Inc., Franklin, NJ) | — | 2 | 2 |
| Sodium Chloride | 4.75 | 4.25 | 4.25 |
| Guar hydroxypropyltrimonium chloride (N-Hance 3196 Polymer) | 0.6 | 0.6 | 0.6 |
| Polyethyleneoxide (Polyox WSR301) | 0.15 | 0.1 | 0.1 |
| Xanthan gum (Keltrol 1000, Kelco Corp.) | 0.2 | 0.2 | 0.2 |
| Hollow microspheres (Expancel 091 WE40 d24, Akzo Nobel) | 0.36 | 0.3 | 00.3 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.8 | — | — |
| Water | Q.S. | Q.S. | Q.S. |
| Benefit Phase Composition | | | |
| Petrolatum (from Quidesa, Mexico) | 64.99 | 65 | 65 |
| Hydrobrite 1000 White Mineral Oil (from WITCO, USA) | 35 | 35 | 35 |
| Cosmetic Pigment, Red 7 Ca Lake | 0.01 | — | — |
| Surfactant Phase: Benefit Phase Ratio | 55:45 | 55:45 | 55:45 |

The compositions described above can be prepared by conventional formulation and mixing techniques. Prepare the structured surfactant phase composition by first adding citric acid into water at 1:3 ratios to form a citric acid premix. Prepare a polymer premix by adding Polyox WSR301 and Xanthan Gum into Trideceth-3 (Example A) or Isosteareth-2 (Example B and Comparative Example). Then, add the following ingredients into the main mixing vessel in the following sequence with agitation: water, N-Hance polymer, Expancel, sodium lauroamphoacetate, sodium trideceth sulfate, sodium sodium lauroamphoacetate, sodium lauryl sulfate, sodium chloride, sodium benzoate, and Disodium EDTA. Add citric acid premix to adjust pH to 5.7±0.2. Add the polymer premix into the main mixing vessel with continuous agitation. Add perfume (Example A) while continuing to agitate until homogeneous.

Prepare the benefit phase composition by first adding petrolatum into a mixing vessel. Heat the vessel to 180° F. (82.2° C.). Then, add Hydrobrite 1000 White mineral oil and cosmetic pigment (Example A) with agitation. Let the vessel cool down with slow agitation to about 110° F. (43.3° C.) and transfer the lipid to a container to cool down to ambient overnight.

A visually distinct multiphase composition of the present invention can be prepared by melting the benefit phase and combining at a specified ratio with a surfactant phase of the present invention in a transparent package while the package is rotated. A multiphase composition of the present invention can also be prepared by optionally melting the benefit phase and combining with a surfactant phase of the present invention in an agitated tank or using agitation from a static mixer to create a dispersion of one phase in the other, then filling the composition into a package.

A multiphase personal care composition should be stable so that when the composition is used, the composition as dispensed is homogenous throughout the life of the product. As well, the multiphase personal care composition should have an attractive appearance throughout its distribution to the trade. Inventors have discovered that when the cleansing phase of the multiphase personal care composition is unstable, as indicated by the Ultracentrifugation "Third Phase" Stability Test below, visible separation of surfactant phases can occur so that inhomogeneity within the package can result, and in addition the appearance of the product in the package can become unsightly, as well as having an unsightly dispensed appearance. Even when coarse separation may not occur, inventors have further discovered that when the cleansing phase of the multiphase personal care composition is unstable, relative movement of areas of the visually distinct composition can occur during, e.g., transportation, thus showing visible evidence of instability in a transparent package when the composition is visually distinct.

Ultracentrifugation "Third-Phase" Stability Test: Structured surfactant phase stability is determined through Ultracentrifugation "Third-Phase" Method as discussed in the Test Methods section above. The example of the present invention and the comparative example is prepared by hand-mixing structured surfactant phase and a benefit phase at 55:45 w/w ratio for 3 minutes vigorously by hand in a 4 oz. jar. The mixture is capped and placed at 120° F. (48.9° C.) for 10 days. After 10 days, a compositionally homogenous aliquot of the mixture is removed and ultracentrifuged. Phase stability is measured after ultracentrifugation at 50,000 rpm for 2 hours at 40° C. The third phase volume is measured. The results are listed in the Table 2 below for Example surfactants of the Present invention sodium lauroamphoacetate, combined with 45% of a benefit phase.

It has been observed that personal care compositions show less phase stability with the formulation and presence of third phase volumes. Typically, as the volume of a third phase increases in a composition, the stability of that composition decreases, i.e., separation of the composition into layers can result. Conversely, personal compositions show improved stability when the compositions have lower third phase volume. Thus, as the volume of a third phase decreases in a composition, the stability of the composition increases. Accordingly, a personal care composition is considered stable when it has less than 7%, preferable less than 5%, most preferably less than 3% third phase and even more preferably 2% third phase.

The results below in Table 2 show that the comparative example of personal care composition is less stable due to formation of high third phase volume. The example of the present invention shows improved phase stability due to lower third phase volume.

TABLE 2

Third Phase Stability of the Example of the Present Invention and Comparative Example

|  | Example A of the Present Invention of Table 1 | Example B of the Present Invention of Table 1 | Comparative Example of Table 1 |
|---|---|---|---|
| Percentage Diacetate | 2.5% | 2.5% | 32% |
| Third Phase Stability: | 0% $3^{rd}$ Phase (stable) | 1% $3^{rd}$ Phase (stable) | 9% $3^{rd}$ phase (not stable) |

Table 3 shows the Percentage Diacetate for examples for the present invention, a comparative example and representative samples of currently marketed body washes.

TABLE 3

Percentage Diacetate of Representative Body Washes

| Examples | Approx. Ratio of Diacetate to Monoacetate | Percentage Diacetate |
|---|---|---|
| Example A of the Present Invention of Table 1 | 0.025 | 2.5% |
| Comparative Example of Table 1 | 0.32 | 32% |
| JOHNSON'S SOFTWASH Extra Care body wash | 0.34 | 34% |
| ST. IVES Whipped Silk Moisturizing Body Wash, Soft Petal Breeze | 0.18 | 18% |
| EQUATE Moisturizing Cleanser with Shea Butter and Vitamins | 0.19 | 19% |
| KROGER Complete 2 in 1 body wash, fresh scent | 0.19 | 19% |
| The Healing Garden, Sensual Therapy 2 in 1, Moisturising Body Wash with Lotion, Jasmine, | 0.42 | 42% |
| TARGET All Day Moisturizing Cleanser-Extra dry | 0.22 | 22% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multiphase personal care composition comprising at least a first phase and a second phase; said first phase comprises a structured surfactant phase comprising at least about 0.5%, by weight of said multiphase personal care composition, of an alkylamphoacetate; wherein said alkylamphoacetate comprises a Percentage Diacetate of less than about 15%.

2. The multiphase personal care composition of claim 1, wherein said alkylamphoacetate is selected from the group consisting of lauroamphoacetate, cocoamphoacetate, and mixtures thereof.

3. The multiphase personal care composition of claim 1, wherein said second phase comprises a benefit phase.

4. The multiphase personal care composition of claim 1, wherein said second phase comprises a structured aqueous phase.

5. The multiphase personal care composition of claim 1, wherein said alkylamphoacetate comprises a Percentage Diacetate of less than about 10%.

6. The multiphase personal care composition of claim 1, wherein said alkylamphoacetate comprises a Percentage Diacetate of less than about 3%.

7. The multiphase personal care composition of claim 1, wherein said structured surfactant phase comprises at least about 1.0%, by weight of said personal care composition, of said alkylamphoacetate.

8. The multiphase personal care composition of claim 1, wherein said structured surfactant phase comprises at least about 2.0%, by weight of said personal care composition, of said alkylamphoacetate.

9. The multi-phase personal care composition of claim 1, wherein said composition further comprises a density modifier, a polymeric phase structurant, or combinations thereof.

10. The multiphase personal care composition of claim 1, wherein said structured surfactant phase further comprises trideceth-3.

11. The multiphase personal care composition of claim 1, wherein said structured surfactant phase further comprises sodium trideceth sulfate.

12. A multiphase personal care composition comprising at least a first phase and a second phase; said first phase comprises a structured surfactant phase comprising at least about 0.5% by weight of said multiphase personal care composition, of sodium lauroamphoacetate, wherein said sodium lauroamphoacetate comprises a Percentage Diacetate less than about 15%.

13. The multiphase personal care composition of claim 12, wherein said sodium lauroamphoacetate comprises a Percentage Diacetate of less than about 3%.

14. The multiphase personal care composition of claim 12, wherein said structured surfactant phase comprises at least about 3.0%, by weight of said personal care composition, of said sodium lauroamphoacetate.

15. The multiphase personal care composition of claim 12, wherein said second phase comprises a benefit phase.

16. The multiphase personal care composition of claim 12, wherein said second phase comprises a structured aqueous phase.

17. The multiphase personal care composition of claim 12, wherein said structured surfactant phase further comprises trideceth-3.

18. The multiphase personal care composition of claim 12, wherein said structured surfactant phase further comprises sodium trideceth sulfate.

19. The multiphase personal care composition of claim 1, wherein said alkylamphoacetate comprises a Percentage Diacetate ranging from about 2.5% to about 15%.

20. The multiphase personal care composition of claim 12, wherein said sodium lauroamphoacetate comprises a Percentage Diacetate ranging from about 2.5% to about 15%.

* * * * *